United States Patent [19]
Wu et al.

[11] Patent Number: 5,760,852
[45] Date of Patent: Jun. 2, 1998

[54] LASER-HARDENED EYE PROTECTION GOGGLES

[75] Inventors: Shin-Tson Wu, Northridge; Chiung-Sheng Wu, Los Angeles; Khoon-Cheng Lim, Agoura; Tsung-Yuan Hsu, Westlake Village, all of Calif.

[73] Assignee: Hughes Electronics Corporation, El Segundo, Calif.

[21] Appl. No.: 552,412

[22] Filed: Nov. 3, 1995

[51] Int. Cl.⁶ .......................... G02F 1/1335; G02B 6/06; G02C 7/10
[52] U.S. Cl. .......................... 349/14; 349/62; 385/119; 385/120; 250/227.11
[58] Field of Search .......................... 349/13, 14, 62, 349/57, 159, 161; 351/44, 45; 385/115, 901, 116, 119, 120; 250/208.1, 227.11, 227.12, 227.2; 345/8, 32

[56] References Cited

U.S. PATENT DOCUMENTS

| | | | |
|---|---|---|---|
| 4,978,208 | 12/1990 | Hsu et al. | 351/45 |
| 5,081,542 | 1/1992 | Efron et al. | 349/14 |
| 5,200,838 | 4/1993 | Nudelman et al. | 358/443 |
| 5,220,164 | 6/1993 | Lieber et al. | 250/214 VT |
| 5,336,900 | 8/1994 | Peters et al. | 250/226 |
| 5,608,833 | 3/1997 | Au et al. | 385/116 |

*Primary Examiner*—William L. Sikes
*Assistant Examiner*—Tai V. Duong
*Attorney, Agent, or Firm*—V. D. Duraiswamy; W. K. Denson-Low

[57] ABSTRACT

An imaging system that can tolerate high intensity optical beams without a reduction in the system's field-of-view, comprises an imager, a fiber array positioned at the image plane of the imager, a sensor array positioned at the output end of the fiber array, a panel display positioned in proximity of the fiber array and an image processor for electronically processing the information from the sensor array.

31 Claims, 4 Drawing Sheets

FIG. 2.
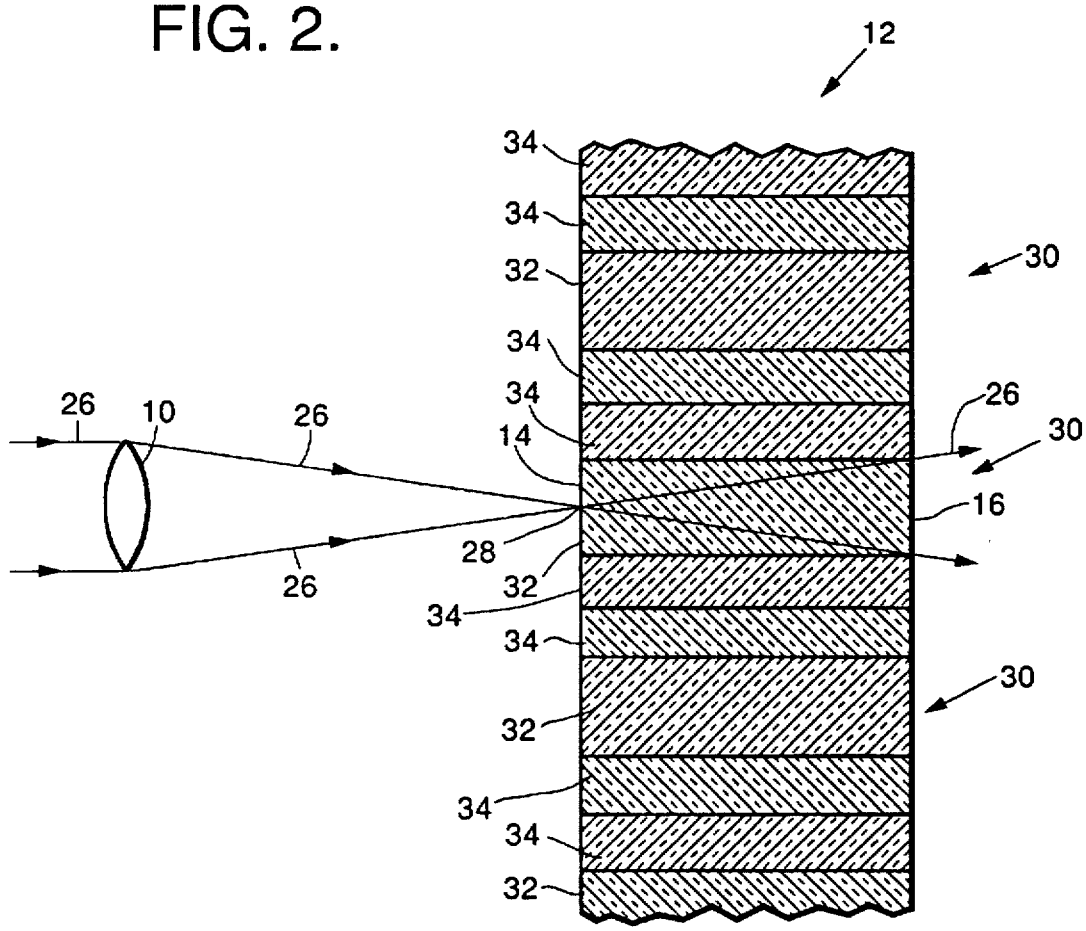
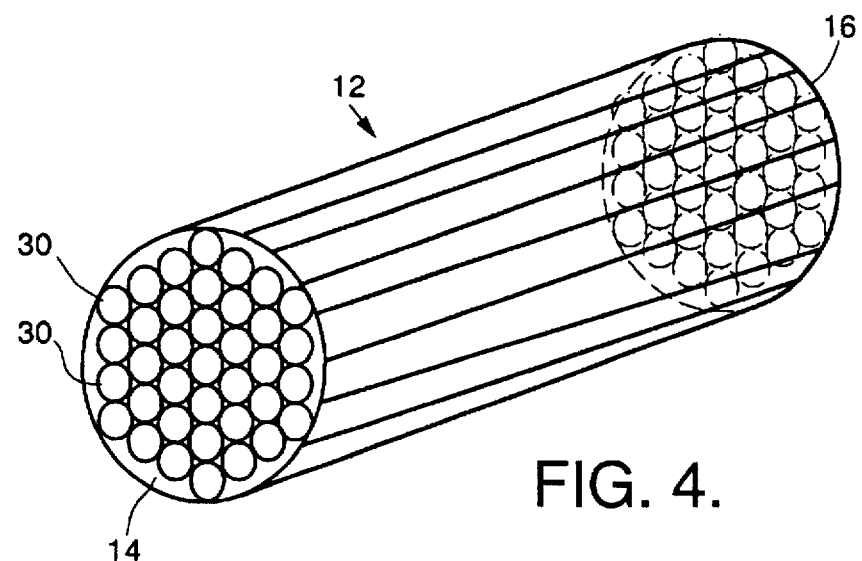
FIG. 4.

LASER-HARDENED EYE PROTECTION GOGGLES

BACKGROUND OF THE INVENTION

1. Field of the Invention

The present invention relates to eye protection devices. More particularly, the present invention relates to laser-hardened eye protection goggles.

2. Description of the Related Art

Laser-hardened eye protection goggles are often used to protect the human eye from exposure to potentially damaging optical radiation, particularly laser radiation. An example is described in U.S. Pat. No. 5,081,542, entitled "LIQUID CRYSTAL LIGHT VALVE GOGGLES FOR EYE PROTECTION", issued Jan. 14, 1992 to Uzi Efron et al., and assigned to Hughes Aircraft Company, the assignee of the present invention. This patent discloses protective goggles that utilize an imaging lens and a photosensitive liquid crystal light valve (LCLV). The imaging lens images objects into the LCLV, and the LCLV reproduces the image in a spectral range to which the human eye is sensitive. The user wearing the goggles views the image through the LCLV, and is thereby shielded from potentially harmful optical radiation.

The LCLVs that are used in these eye-protection devices function basically as image detectors. The typical image detector, particularly the LCLV used in the device described above, has a relatively low optical damage threshold. The image detector is typically positioned at the image plane of the imaging lens so that an incoming optical beam will be focused onto the image detector. This results in an optical intensity level that can very easily damage the detector and render the imaging device inoperative.

One way to reduce the optical intensity at the image detector is to increase the diameter of the focused optical beam (increase the focal spot diameter), which can be accomplished by using an imaging lens with a large f-number, the ratio of the focal length to the aperture of the lens. However, as the f-number of the imaging lens is increased, the sensitivity of the device is reduced. In addition, although the LCLV goggle protects both cw and pulsed laser threats, the photosensitivity of this device is not sufficient to cover the entire daylight ambient, and its dynamic range is too narrow at a fixed operation frequency. Moreover, to erect the inverted image in a LCLV device, a fiber twister is commonly used. This can increase the device's weight, size and cost.

Camcorder view-finders which typically incorporate charge-coupled devices (CCD) with liquid crystal displays (LCD) or cathode ray tube (CRT) provide many features that would be beneficial in providing eye protection. Similar to a LCLV goggle, CCD-LCD view finders can be used for protecting cw and pulsed, as well as multi-wavelength laser threats. Its spectral response spans from UV to 1.1 μm. The image erection in the CCD-LCD view-finder is corrected by an electronic means. Moreover, this device exhibits a high sensitivity and wide dynamic range.

However, several problems have inhibited the use of CCD-LCD view-finder principles from being incorporated into eye-protection devices. For example, a compact packaging must be designed. Also, there is the problem of low damage threshold. Further, the dynamic range of CCD-based goggles is still limited. Even at a threat intensity far below the damage threshold, a localized blooming may occur. This blooming usually appears as stripes. This is due to the excessive charge overflow along the stripes. Thus, there is a need for an eye-protection device that overcomes the above-described problems.

SUMMARY OF THE INVENTION

The present invention provides an imaging system including an imager, an optical fiber array positioned at the image plane of the imager, a sensor array positioned at the output end of the fiber array, a panel display physically separate from the sensor array and an image processor. The optical fibers making up the fiber array have a length such that the diameter of a focused optical beam at the input end of the fiber array is substantially smaller than the diameter of the optical beam at the output end of the fiber array.

In accordance with a preferred embodiment of the present invention, the fiber array transfers the imaged scene to the sensor array at its output end. The focused optical beam is coupled into one of the fibers of the fiber array and is also transferred to the image detector at the fiber array's output end. The angular divergence of the optical beam causes its diameter to increase as it propagates through the fiber. The length of the optical fibers in the fiber array is chosen such that, at the output end of the fiber array, the diameter of the optical beam substantially equals the diameter of the fiber that guided it. The larger optical beam diameter results in lower optical intensity at the sensor array.

Since the fiber array is typically less expensive to replace than the sensor, the f-number of the imaging lens and the diameter of the fiber cores are preferably designed so that, as the power of an incoming optical beam increases, the optical damage threshold of the fiber array is reached before that of the sensor array. In addition, the fiber core diameters are preferably smaller than the image resolution of the sensor array, so that the resolution of the imaging device is not limited by the fiber core diameters. Moreover, the fact that the sensor array is physically separated from the panel display ensures that a laser threat does not reach the eye.

The invention itself, together with further objects and attendant advantages, will best be understood by reference to the following detailed description, taken in conjunction with the accompanying drawings.

BRIEF DESCRIPTION OF THE DRAWINGS

FIG. 2 is a sectional view of the fiber array of FIG. 1.

FIG. 4 is a perspective view of a substantially straight fiber array used in the embodiment of FIG. 3.

DESCRIPTION OF THE PREFERRED EMBODIMENTS

Figure 1:
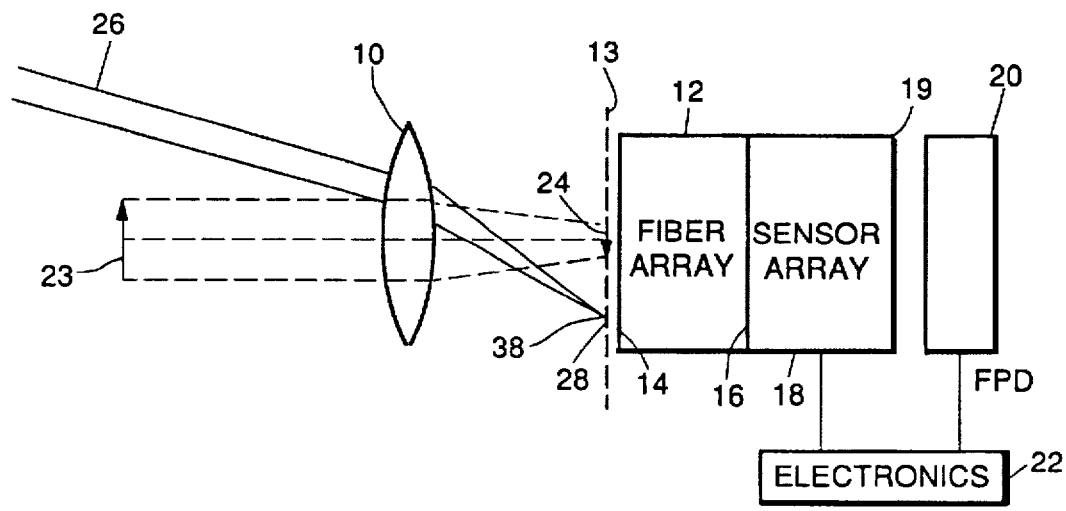
FIG. 1 is a schematic diagram illustrating the basic principles of the invention.

FIG. 1 illustrates the basic principles of the invention. An imager 10, preferably a lens, is used to image a scene under observation, represented by arrow 23. A fiber array 12 is positioned at the image plane 13 of lens 10, and a sensor array 18 is positioned at the output end 16 of the fiber array 12. A panel display 20 is positioned near the output end 19 of the sensor array. An image processor 22 (denoted "Electronics") is positioned in the proximity of the sensor array 18 and the panel display 20.

In FIG. 1, the image plane 13 is shown slightly offset from the input end 14 of fiber array 12 for ease of illustration. In practice, the fiber array's input end 12 and the image plane 13 lie in substantially the same plane. The fiber array 12 includes an array or a bundle of individual glass optical fibers (not shown). Fiber arrays are well known and are commercially available from, for example, Galileo Optics. The sensor array 18 includes a plurality of sensor elements (not shown).

In operation, the scene under observation 23 is imaged at image plane 13. In practice, the distance from scene 23 to lens 10 is large enough relative to the focal length of lens 10 that the image plane 13 is located at the lens' focal plane. The image 24 will generally extend over a number of fibers in the fiber array 12, so that each illuminated fiber captures a portion of image 19 (an image pixel) and guides it to is the fiber array's output end 16, where it is detected by sensor array 18.

If a collimated optical beam 26, such as a laser beam powerful enough to damage the user's eyes, is positioned within the field-of-view of lens 10 and directed towards lens 10, it is focused to a spot 28 at the focal plane (the image plane 13 in practice) of lens 10. The fiber array 12 is chosen so that the individual fibers (not shown) have core diameters that are larger than the expected diameter of beam 26 at image plane 13 (the focal spot 28 in practice). The term "collimated optical beam" does not necessarily refer to a beam made up of perfectly parallel rays (or a perfectly planar wavefront). Rather the term is used to refer to an optical beam with a wavefront that is sufficiently planar at lens 10 to be focused to a spot 28 that is smaller than the fibers in fiber array 12.

Focused beam 38 is captured by one of the fibers in the fiber array 12 and guided to the fiber array's output end 16, as illustrated in FIG. 2. The divergence of the focused beam 38 as it propagates through the core 32 of one of the fibers 30 causes its diameter to increase. The length of the fibers 30 in fiber array 12 is chosen so that, at the array's output end 16, the diameter of focused beam 38 (output diameter) substantially equals the diameter of the fiber 30 that guided it. The fiber array 12 is chosen so that each individual fiber 30 has a core 32 with a diameter that is larger than the diameter of focused beam 38 at the fiber array's input end 14 (input diameter), with each fiber core 32 surrounded by the fiber's cladding 34.

In the preferred embodiment, the fiber core and cladding are made of silica. When the fiber array's input end 14 is positioned at the focal spot 28 of focused beam 38, and when the beam's propagation direction is parallel to the fiber's longitudinal axis (0 degree angle of incidence), the focused beam's diameter (ω) at the fiber array's output end 16 is a function of the length (z) of the fiber 30 that guides it, and can be calculated with the following equation:

$$\omega(z) = \omega_o \sqrt{1 + \left[\frac{\lambda z}{\pi \omega_o}\right]^2} \quad (1)$$

where $\omega_o$ is the focused beam diameter at focal spot 28, and λ is the beam's wavelength. The length (z) of each fiber 30 in the array is preferably chosen so that the diameter of the focused beam 38 that is incident on the fiber array 12 with a 0 angle of incidence has a diameter that is substantially equal to the diameter of the fiber core 32 at the fiber array's output end 16. For example, if $\omega_o$ is 2.5 microns, the wavelength of beam 26 is 0.55 microns, and the diameter of the fiber core is 10 microns, then the length of fiber 30 must be at least approximately 143 microns for beam 26 (with a 0 degree angle of incidence) to have a diameter that is equal to the core diameter (10 microns) at the fiber array's output end 16.

Focused optical beams that are incident on the fiber 30 at oblique angles (with propagation directions that are not parallel to the fiber's longitudinal axis) will internally reflect from the sides of the fiber core 32 and will travel longer distances than a focused beam that is incident on the fiber 30 at 0 degrees. Therefore, their diameters will also equal the diameter of the fiber core 32 at the fiber array's output end 16.

The increased diameter of the focused beam 38 results in lower optical intensity at the fiber array's output end 16 than at the input end 14, which reduces the optical intensity experienced by sensor array 18. On the other hand, the image 24 of scene 23 will spread over the input areas of the multiple fibers in the fiber array 12. The sensor array 18 thus detects background image beams without significant loss of intensity, while at the same time greatly reducing the intensity of high power laser beams.

If optical beam 26 fills the entire aperture of lens 10, and has a Gaussian intensity profile, lens 10 will focus it to a diffraction-limited spot size $\omega_o$ given by:

$$\omega_o = \frac{2\lambda(f\#)}{\pi} \quad (2)$$

where f# is the f-number of the lens. For a lens 10 with an f-number of 1.25, an optical beam 26 with a wavelength of 0.53 microns that fills the entire aperture of lens 10, beam 26 will focus down to a diffraction-limited spot size of 0.42 microns. In practice, the diffraction-limited spot size cannot be achieved because of lens tolerances and optical turbulence. The applicants have found that the above parameters will yield a spot size greater than about 1 micron at the fiber array's input side 14.

For a 1 micron spot size at the array's input side 14, and a fiber core diameter of 5 microns, the optical intensity at the fiber array's output side 16 will be roughly 25 times less than the intensity at the array's input side 24. This is because the optical intensity is inversely proportional to the square of the radius of optical beam 26. In the preferred embodiment, the f-number of lens 10 and the diameters of the fibers in the fiber array 12 are chosen so that as the power of beam 26 increases, the optical intensity at the fiber array's input end 14 will exceed the fiber array's damage threshold before the optical intensity at the fiber array's output end 16 exceeds the damage threshold of sensor array 18. If a sufficient number of fibers in the fiber array 12 are optically damaged during operation, the fiber array 12 may be replaced. Replacing the fiber array 12 will typically be much less costly than replacing the sensor array 18. Preferably, a tapered fiber array can be used for increasing the field-of-view.

The sensor array 18 contains sensor elements (not shown) made of a solid state photosensing material, such as silicon. In a preferred embodiment of the present invention, the core diameter of the individual fibers 30 results in a surface area that is similar to the surface area of the sensor elements. In addition the fiber array 12 contains a sufficient number of individual fibers to cover all of the sensor elements. Preferably, the sensor array contains a highly sensitive thin-film-photo-transistor (TFPT) array, or a well-known charge-coupled device (CCD). In a TFPT, the sensor elements are pixelized elements making up a black matrix.

It is also preferred that the sensor array is positioned in contact with the fiber array 12 to avoid loss of resolution.

The image 24 detected by sensor array 18 is sent to an image processor 22 to be inverted and otherwise processed for displaying by the panel display 20.

Figure 3:
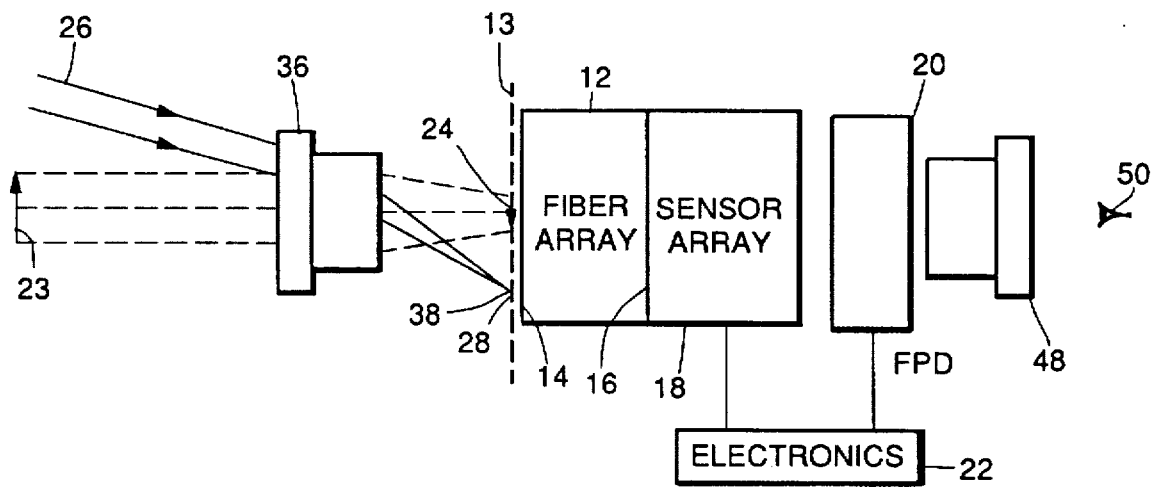
FIG. 3 is a schematic diagram illustrating a preferred CCD-LCD imaging system that incorporates the present invention.

A more detailed representation of a CCD-LCD imaging system that incorporates the present invention is shown in FIG. 3. An objective lens 36 is used as the imaging lens. As explained above, an observed scene 23 is imaged at the input end 14 of a fiber array 12. As in FIG. 1, the image plane 13 is shown slightly offset from the array's input end 14 for illustration purposes only. The fiber array 12 operates as described above in connection with FIGS. 1 and 2.

The image 24 is guided along the fibers that make up the fiber array 12 to the fiber array's output end 16. The fiber array 12 is preferably a straight fiber array, as illustrated in FIG. 4, in which the fibers 30 that make up the array are substantially parallel to the longitudinal axis so that the orientation of the image at the output end 16 of the fiber array 12 is the same as its orientation at the input end 14 of the array 12. In a preferred embodiment, the fiber array 12 employed is a fiber face plate. A fiber face plate includes a set of individual fibers that are fused together. Such a fiber faceplate is made of glass or quartz, which is much more resistant to laser damage than the silicon material making up the photosensor elements in the sensor array 18.

For example, the spot diameter of an objective lens with f#=1.2 is about 2.5 µm at a visible wavelength. If this light is focused onto the sensor array directly, the photosensor element could be damaged easily. To enhance the damage threshold of photosensor, a thin fiber bundle faceplate is placed in the focal plan of the objective lens. The spot size diverges as the beam propagates through the fiber according to equation (1). Assuming that each sensor pixel is 10 µm by 10 µm, the multimode fiber diameter should be limited to d=10 µm in order to not lose resolution. The laser beam will diverge to fill the whole fiber after propagating a 143 µm distance. Therefore, the minimum fiber faceplate thickness is t=143 µm. For safety and weight considerations, a 1 mm thick fiber faceplate with 10 µm fiber diameter is preferable.

Another method for uniformly diverging a laser beam is to use the Gradient-Index (GRIN) lens. The length of a GRIN lens is crucial in determining the output beam profile. For example, a one-pitch length GRIN lens refocuses the input beam to its original size at the exit, and the 0.25 pitch lens not only uniformly expands but also collimates the output beam. Under this circumstance, the GRIN lens needs not be in proximity contact with the photosensor array. This feature is particularly important because the finished sensor array is usually overcoated with a thin protecting layer, such as glass, on its surface.

With the insertion of such a fiber faceplate or GRIN lens, the laser intensity arriving at photosensor is reduced by a factor of 16. If the damage threshold of C—Si is within 16 times of the fiber or GRIN lens employed, then the damage would occur at the faceplate, but not at the photosensor. Replacing a fiber faceplate is easier and less costly than replacing a photosensor array. The transmission loss of such a faceplate is about 20%.

In another preferred embodiment, a diamond film (not shown) is placed between the fiber array 12 and the sensor array 18 to enhance the damage threshold of the sensor array. The diamond film has a large thermal conductivity and thus helps to dissipate the heat generated by a laser beam.

The electronic output signals of the sensor array 12 is regulated by an image processor 22 so that the electronic gain can be controlled either automatically or manually. This electronic device also serves to erect the inverted image originating from the objective lens 36. Normally, correction of the inverted image is achieved by using a 180°-twisted fiber bundle. Such twisted fibers are expensive, heavy weight and thus undesirable for a helmet-mounted goggle. Thus, the image processor 22 utilized in the present invention results in a compact, light weight, low cost and high performance eye protection goggle.

In a preferred embodiment of the present invention, the image processor 22 is equipped with an electronic circuit to convert linear video signals from a sensor array such as a CCD array to a different scale such as a logarithmic scale before driving the panel display 20. This simple circuit significantly improves the dynamic range of the device. Thus, for example, the image processor 22 preferably contains an electrical signal amplifier which converts the incoming linear signal into logarithmic signals, a register circuitry to transfer the information obtained by the CCD array into video signals and a power supply to power the CCD.

The panel display 20 preferably includes a flat panel display (FPD), such as a thin-film-transistor liquid crystal device. Preferably, the panel display 20 is a high resolution flat panel display device, such as a transmissive mode thin-film-transistor (TFT) liquid crystal device (LCD) with back-lighting. To save space, a thin-film electroluminescent device is preferably employed as back-light for LCD. Alternatively, a self-emissive display can be used for displaying images. For a device that displays color, both color sensor array such as color CCD and color display such as color LCD can be used.

Both amorphous, polycrystalline and crystalline silicon Thin-Film-Transistors have been used extensively in display industries. These transistors are highly light sensitive and hence can be used also as TFPT. A focal plan array of TFPT is similar to the TFT array substrate used for display. It consists of arrays of TFPT that are being addressed individually by X, Y address lines. Preferably, each TFPT pixel is made larger than the standard TFT for greater sensitivity. Each pixel works as an independent photosensor.

Photosensitivity and gain of the TFPT array can be controlled pixel by pixel by electronic means. These pixels are isolated by black matrices. Thus, the breakdown will be localized. Further, individually addressed pixel would also eliminate the stripe breakdown problem caused by the line addressing scheme in CCD. The TFPT-based goggle has pixelized resolution elements. During the laser threat, only a limited number of pixels are blurred, it still retains see-through capability over the rest of the field-of-view. In addition, the TFPT arrays can provide optical gain through the voltage applied to the transistor so that its sensitivity is about one order of magnitude better than a CCD.

The advantages of the TFPT focal plane arrays are found in the following areas:

(1) Improved sensitivity (each TFPT acts also as an amplifier)

(2) Wider Dynamic range (individually controlled pixel operating voltage)

(3) Improved breakdown (not permanent damage) threshold, and (4) Suppressed washed-out image.

Because the intensity of focused optical beam 38 is greater at the fiber array's input end 14 than at its output end 16, the optical damage threshold of fiber array 12 will be reached before that of sensor array 18. Even if the sensor array is damaged, one can simply replace the sensor elements. All of the driving electronics of the sensor circuit and the high resolution TFT-LCD display panels do not need to be changed. This greatly reduces the repair cost. Moreover, because the sensor array 18 is physically separate from the panel display 20, a laser threat would not reach the viewer 50.

The advantages and other characteristics of the present invention are best illustrated by the following examples.

EXAMPLES 1-4

The sensitivity of two black/white CCD-LCD monoculars was compared to that of the human eye and a 700-line 0.60 inch cathode ray tube. LCD1 contained a CCD array having 512(H)×494(V) pixels with black/white sensitivity and a liquid crystal display having 800(H)×480(V) pixels in 1.35 inch diagonal. LCD2 contained the same CCD array as LCD1 and a liquid crystal display having 800(H)×225(V) pixels in 0.70 inch diagonal.

Figure 5:
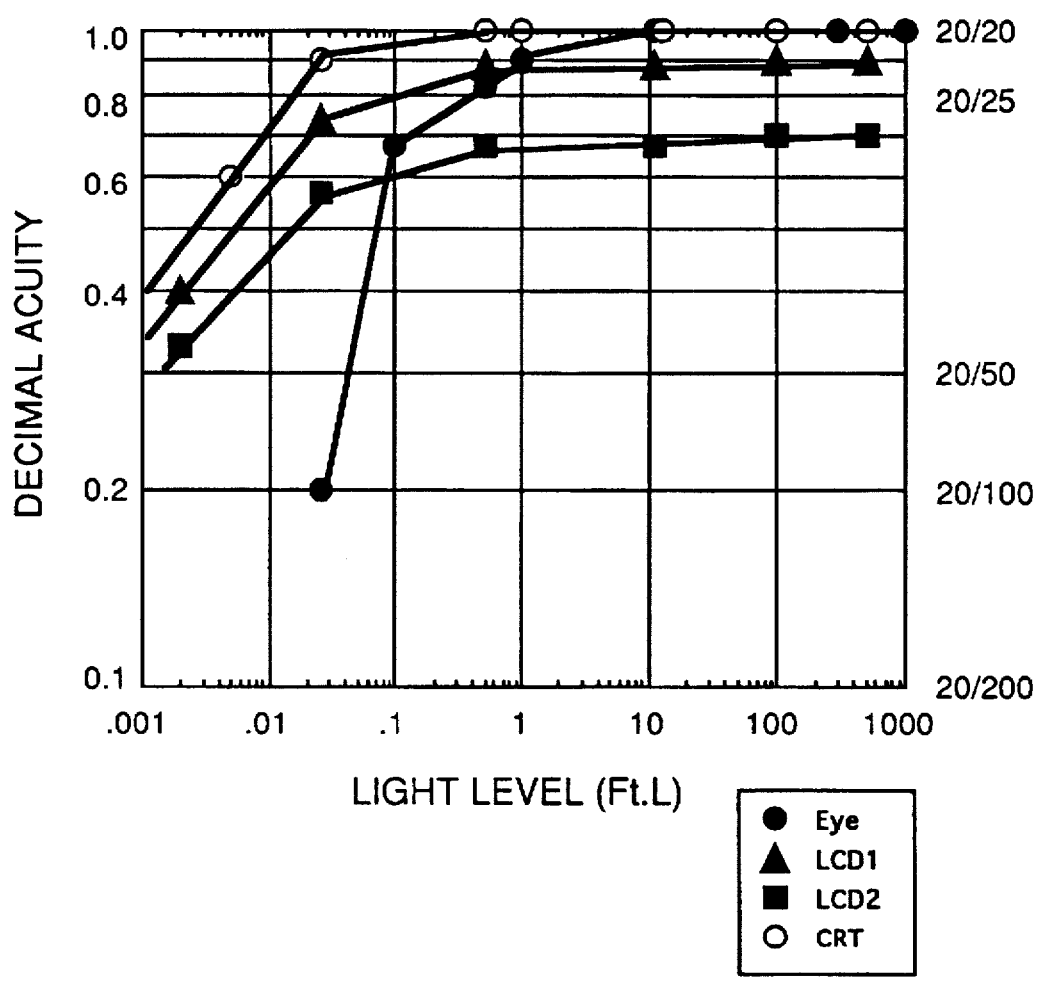
FIG. 5 is a graph showing the decimal accuity at different light levels of two black/white CCD-LCD monocular in accordance to the present invention.

The results are shown in FIG. 5.

The following characteristics were observed from examples 1-4:

1. Photosensitivity

The sensitivity of the CCD array can be adjusted by controlling the electronic gain and the f-number of the objective lens. Using an f1.4 objective lens, the sensitivity of the CCD camera was measured to be about 0.005 Foot-Lambert which is about 1000 times more sensitive than our present LCLV goggle. Such a CCD-based goggle will be useful from dawn to dusk, covering the entire day light conditions.

2. Dynamic Range

The usable dynamic range of a CCD camera is about 6 orders. At a given setting, the dynamic range was measured to be about 100, which is 20 times wider than the Hughes LCLV goggle.

3. Spectral Bandwidth

The spectral response of CCD spans from UV to 1.1 μm which is useful for protecting agile-frequency and multi-wavelength laser threats. This device can also work as a near IR goggle.

4. Resolution

Presently, CCD arrays with 1024×1024 pixels or larger are commercially available. The high resolution, small-size TFT-LCD panels have been demonstrated worldwide for HDTV projectors. Thus, both key components in this invention will be available commercially soon at a reasonably low cost.

5. Response Time

The frame rate of a CCD is about 30 Hz. No image lagging was observed.

EXAMPLES 5-7

The sensitivity of a two color CCD-LCD monoculars was compared to that of the human eye. LCD3 is a device containing a CCD having 510×492 pixels and a LCD having 800×480 dots. LCD4 is a device containing the same CCD as LCD3 and a LCD having 800×225 dots.

Figure 6:
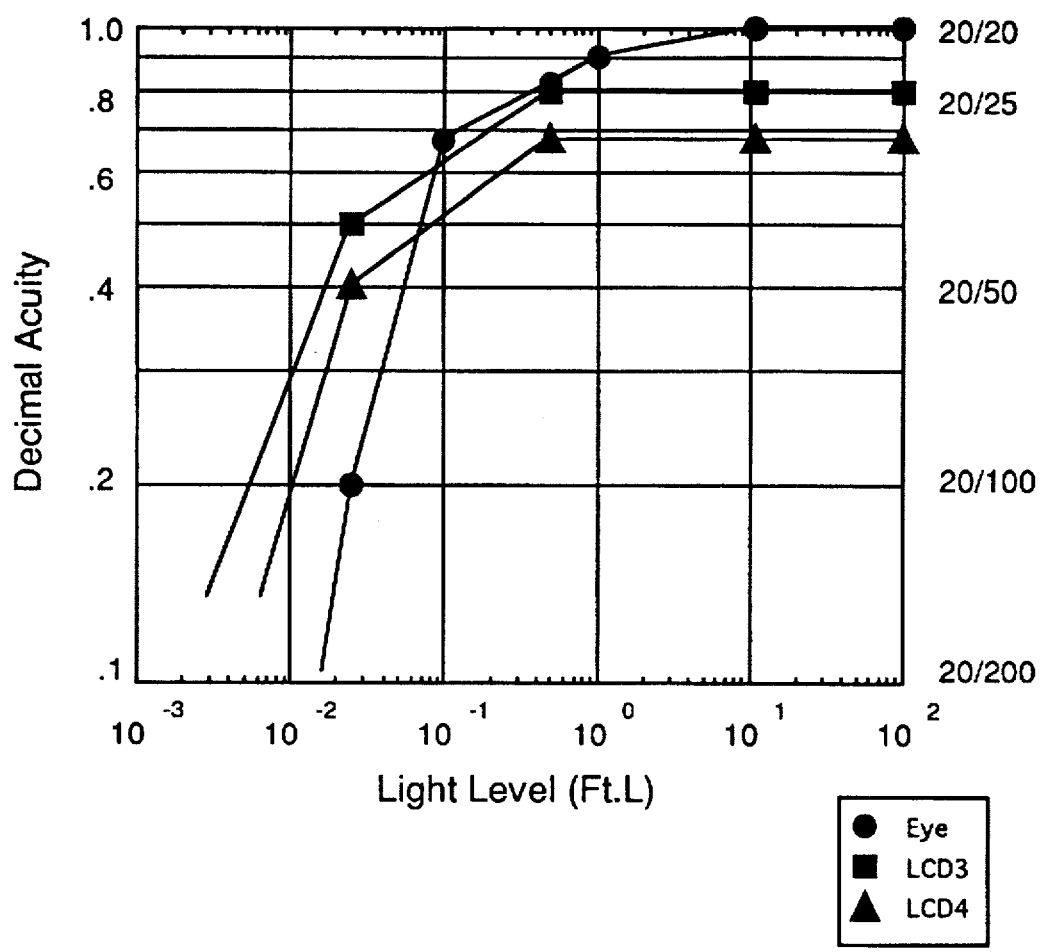
FIG. 6 is a graph showing the decimal accuity at different light levels of two color CCD-LCD monoculars in accordance to the present invention.

The result is shown in FIG. 6.

It can be seen from examples 5-7 that the color CCD-LCD does not have high enough acuity as the human eye at light level greater than 0.1 Foot-Lambert (Ft.L.). But below 0.1 Ft.L., the color CCD-LCD shows higher resolution and better sensitivity than the human eye.

The present invention overcomes the low damage threshold problem of a CCD-LCD and preserves all the favorable features. Thus, the improved device will be useful for protecting eye from being damaged by laser threats.

A sensor array containing a thin-film-photo-transistor (TFPT) array would eliminate stripe breakdown problem since the TFPT-based goggle have pixelized resolution elements. Because each pixel works as an independent detector, the photosensitivity and gain can be controlled pixel by pixel by electronic means. These pixels are isolated by black matrices. Thus, the breakdown will be localized. During a laser threat, only a limited number of pixels are blurred, it still retains see-through capability.

In addition, the thin-film-photo-transistor array can provide optical gain through the voltage applied to the transistor so that its sensitivity is better than a CCD. The format of the goggle may be hand-held or head-mounted.

Of course, it should be understood that a wide range of changes and modifications can be made to the preferred embodiment described above. It is therefore intended that the foregoing detailed description be regarded as illustrative rather than limiting and that it be understood that it is the following claims, including all equivalents, which are intended to define the scope of this invention.

What is claimed is:

1. An imaging system comprising:
    an imager positioned to create an image of a scene and to focus an incident collimated optical beam onto an image plane;
    a fiber array having an input end and an output end, said input end positioned at said image plane so that said fiber array captures the image and the focused optical beam and guides them to the output end, said fiber array including a plurality of optical fibers, said focused optical beam having an input diameter at the input end and an output diameter at the output end;
    a sensor array positioned at the output end of said fiber array so that said sensor array captures said image and focused optical beam from the output end of the optical fiber array and generates output signals, said sensor array including sensor elements comprising a solid state photosensor material, said sensor elements having a surface area;
    an image processor for processing the image and focused optical beam from the sensor array;
    a panel display, separately positioned from the sensor array, for reading the processed image and optical beam from the image processor;
    wherein each optical fiber has a length such that the output diameter of the focused optical beam is substantially greater than the input diameter of the focused optical beam.

2. The imaging system of claim 1 wherein the image from the sensor array is an inverted image and the image processor erects said inverted image.

3. The imaging system of claim 1 wherein the output signals from the sensor array is in a linear form and the image processor converts said optical beam into a logarithmic form.

4. The imaging system of claim 1 wherein said optical fibers are substantially straight.

5. The imaging system of claim 1 wherein said fiber array is a gradient index lens.

6. The imaging system of claim 1 wherein said sensor array includes thin film phototransistors.

7. The imaging system of claim 1 wherein said sensor array includes a charge-coupled device.

8. The imaging system of claim 6 wherein said thin film phototransistor is a black matrix/metal-type phototransistor comprising a plurality of pixelized elements, said pixelized element having a pixel size.

9. The imaging system of claim 1 wherein the optical fibers have a fiber surface area substantially equal to the surface area of the sensor elements.

10. The imaging system of claim 1 further comprising a diamond film array between the fiber array and the sensor array.

11. The imaging system of claim 1 wherein the panel display includes of a flat panel display device.

12. The imaging system of claim 11 wherein the flat panel display device is a thin-film-transistor liquid crystal device.

13. The imaging system of claim 11 wherein the flat panel display device is a high resolution flat panel display.

14. The imaging system of claim 11 wherein the flat panel display device is a transmissive mode thin-film-transistor liquid crystal device with a back-lighting.

15. The imaging system of claim 11 wherein the panel display further includes a thin-film electroluminescent device.

16. The imaging system of claim 1 wherein the panel display includes a self-emissive display.

17. A method for protecting a viewer from a laser threat, the steps comprising placing the imaging system of claim 1 between the laser threat and the viewer.

18. An eye protection device wherein an objective lens creates an image and focuses an incident collimated optical beam at a image plane, comprising:
 a fiber faceplate having an input end and an output end, said input end positioned at said image plane so that the fiber faceplate captures the image and the focused optical beam and guides them to its output end, said fiber faceplate including a plurality of optical fibers;
 a photosensor array positioned at the output end of said fiber faceplate, so that said photosensor array captures said image and focused optical beam from the output end of the fiber faceplate and generates output signals, said photosensor array including sensor elements comprising a solid state material having a solid state damage threshold, said photosensor array outputing an electronic gain;
 an image processor comprising an electronic circuitry capable of allowing control of the output signals from the photosensor array, wherein said electronic circuitry processes the image and focused optical beam from the photosensor array;
 a display device positioned in close proximity to said solid state photosensor array for reading the processed image and optical beam from the image processor.

19. The eye protection device of claim 18 wherein the optical fibers in said fiber faceplate have a damage threshold greater than the solid state damage threshold.

20. The eye protection device of claim 18 wherein the image from the sensor array is an inverted image and the image processor erects said inverted image.

21. The eye protection device of claim 18 wherein the output signals from the sensor array is in a linear form and the image processor converts said focused optical beam into a logarithmic form.

22. The eye protection device of claim 18 wherein said optical fibers are substantially straight.

23. The eye protection device of claim 18 wherein said fiber array is a gradient index lens.

24. The eye protection device of claim 18 wherein said sensor array includes thin film phototransistors.

25. The eye protection device of claim 18 wherein said sensor array includes a charge coupled device.

26. The eye protection device of claim 24 wherein said thin film phototransistor is a black matrix/metal-type phototransistor comprising a plurality of pixelized elements.

27. The eye protection device of claim 26 wherein:
 the optical fibers have a fiber surface area;
 the sensor elements have an element surface area substantially equal to said fiber surface area.

28. The eye protection device of claim 18 wherein the panel display is a transmissive mode, high resolution flat panel display device.

29. The eye protection device of claim 28 wherein the panel display includes a thin-film-transistor liquid crystal device.

30. The eye protection device of claim 29 wherein the panel display further includes a thin-film electroluminescent device.

31. The eye protection device of claim 18 wherein the panel display includes a self-emissive display.

* * * * *